US00PP19721P2

(12) United States Plant Patent
Westhoff

(10) Patent No.: US PP19,721 P2
(45) Date of Patent: Feb. 17, 2009

(54) ***LANTANA* PLANT NAMED 'WESLAMO'**

(50) Latin Name: *Lantana camara*
Varietal Denomination: Weslamo

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 12/079,310

(22) Filed: Mar. 25, 2008

(51) Int. Cl.
*A01H 5/00* (2006.01)

(52) U.S. Cl. ..... Plt./263.1

(58) Field of Classification Search ..... Plt./263.1, Plt./263

See application file for complete search history.

*Primary Examiner*—Annette H Para
(74) *Attorney, Agent, or Firm*—C. A. Whealy

(57) ABSTRACT

A new and distinct cultivar of *Lantana* plant named 'Weslamo', characterized by its compact, upright and mounding plant habit; vigorous growth habit; durable, dark green-colored leaves; freely flowering habit; and flowers that are held above the foliage in compact inflorescences and are initially yellow becoming orange and eventually dark pink in color.

1 Drawing Sheet

Botanical designation: *Lantana camara.*
Cultivar denomination: 'Weslamo'.

BACKGROUND OF THE INVENTION

The present invention relates to a new and distinct cultivar of *Lantana,* botanically known as *Lantana camara,* and hereinafter referred to by the name 'Weslamo'.

The new *Lantana* is a product of a planned breeding program conducted by the Inventor in Südlohn, Germany. The objective of the breeding program is to create new freely branching *Lantana* cultivars with attractive flower coloration.

The new *Lantana* originated from a cross-pollination made by the Inventor in 2000 in Südlohn, Germany of a proprietary selection of *Lantana camara* identified as code number 00PL3, not patented, as the female, or seed, parent with a proprietary selection of *Lantana camara* identified as code number 00PL6, not patented, as the male, or pollen, parent. The new *Lantana* was discovered and selected by the Inventor as a single flowering plant within the progeny of the stated cross-pollination in a controlled environment in S üdlohn, Germany in 2001.

Asexual reproduction of the new *Lantana* by vegetative cuttings in a controlled environment in Südlohn, Germany since 2001, has shown that the unique features of this new *Lantana* are stable and reproduced true to type in successive generations.

SUMMARY OF THE INVENTION

The cultivar Weslamo has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Weslamo'. These characteristics in combination distinguish 'Weslamo' as a new and distinct cultivar of *Lantana:*

1. Compact, upright and mounding plant habit.
2. Vigorous growth habit.
3. Durable dark green-colored leaves.
4. Freely flowering habit.
5. Flowers that are held above the foliage in compact inflorescences and are initially yellow becoming orange and eventually dark pink in color.

Plants of the new *Lantana* can be compared to plants of the female parent selection. Plants of the new *Lantana* differ from plants of the female parent selection in the following characteristics:

1. Plants of the new *Lantana* are more compact than plants of the female parent selection.
2. Plants of the new *Lantana* are more freely branching than plants of the female parent selection.
3. Plants of the new *Lantana* have smaller leaves than plants of the female parent selection.
4. Plants of the new *Lantana* have more compact inflorescences with larger flowers than plants of the female parent selection.
5. Flowers of plants of the new *Lantana* are yellow becoming orange and eventually dark pink in color whereas flowers of plants of the female parent selection are yellow becoming orange in color with development.

Plants of the new *Lantana* can be compared to plants of the male parent selection. Plants of the new *Lantana* differ from plants of the male parent selection in the following characteristics:

1. Plants of the new *Lantana* have more compact inflorescences than plants of the male parent selection.
2. Flowers of plants of the new *Lantana* are yellow becoming orange and eventually dark pink in color whereas flowers of plants of the male parent selection are orange becoming red in color with development.

Plants of the new *Lantana* can be compared to plants of the *Lantana* cultivar Dallas Red, not patented. In side-by-side comparisons conducted in Südlohn, Germany, plants of the new *Lantana* differed from plants of the cultivar Dallas Red in the following characteristics:

1. Plants of the new *Lantana* were larger and more vigorous than plants of the cultivar Dallas Red.
2. Plants of the new *Lantana* were more freely branching than plants of the cultivar Dallas Red.
3. Plants of the new *Lantana* had larger leaves than plants of the cultivar Dallas Red.
4. Plants of the new *Lantana* had larger inflorescences than plants of the cultivar Dallas Red.
5. Plants of the new *Lantana* and the cultivar Dallas Red differed in flower color as plants of the cultivar Dallas Red initially had yellow-colored flowers that became deep red with development.

Plants of the new *Lantana* can also be compared to plants of the *Lantana* cultivar Balucgold, disclosed in U.S. Plant Pat. No. 14,634. In side-by-side comparisons conducted in S üdlohn, Germany, plants of the new *Lantana* differed from plants of the cultivar Balucgold in the following characteristics:

1. Plants of the new *Lantana* had larger leaves than plants of the cultivar Balucgold.
2. Plants of the new *Lantana* had larger inflorescences and flowers than plants of the cultivar Balucgold.
3. Plants of the new *Lantana* and the cultivar Balucgold differed in flower color as plants of the cultivar Balucgold had yellow-colored flowers.

BRIEF DESCRIPTION OF THE PHOTOGRAPHS

The accompanying colored photographs illustrate the overall appearance of the new *Lantana*, showing the colors as true as it is reasonably possible to obtain in colored reproductions of this type. Colors in the photographs may differ slightly from the color values cited in the detailed botanical description which accurately describe the colors of the new *Lantana*.

The photograph at the top of the sheet comprises a side perspective view of a typical flowering plant of 'Weslamo' grown in a container.

The photograph at the bottom of the sheet is a close-up view of typical inflorescences and leaves of 'Weslamo'.

DETAILED BOTANICAL DESCRIPTION

The aforementioned photographs and following observations and measurements describe plants grown in Südlohn, Germany, under commercial practice during the autumn in a glass-covered greenhouse with day temperatures ranging from 16° C. to 20° C., night temperatures ranging from 16° C. to 18° C. and light levels ranging from 3,000 to 50,000 lux. Plants used in the photographs were about 25 weeks from planting and plants used for the description were about 30 weeks from planting. Plants used for the photographs and for the description were grown in 12-cm containers. In the following description, color references are made to The Royal Horticultural Society Colour Chart, 2001 Edition, except where general terms of ordinary dictionary significance are used.

Botanical classification: *Lantana camara* cultivar Weslamo.

Parentage:

*Female, or seed, parent.*—Proprietary selection of *Lantana camara* identified as code number 00PL3, not patented.

*Male, or pollen, parent.*—Proprietary selection of *Lantana camara* identified as code number 00PL6, not patented.

Propagation:

*Type.*—By vegetative cuttings.

*Time to initiate roots, summer.*—About two to three weeks at 20° C.

*Time to initiate roots, winter.*—About 23 to 30 days at 20° C.

*Time to produce a rooted young plant summer.*—About 30 to 35 days at 20° C.

*Time to produce a rooted young plant, winter.*—About five weeks at 20° C.

*Root description.*—Fibrous; medium in thickness; color, close to 158A.

*Rooting habit.*—Freely branching; moderately dense to dense.

Plant description:

*Plant habit.*—Compact, upright and mounding plant habit; vigorous growth habit. Freely branching habit; typically two lateral branches develop per node; pinching enhances lateral branch development; dense and bushy plant habit.

*Plant height.*—About 12 cm to 17 cm.

*Plant diameter.*—About 27 cm by 31 cm.

Lateral branch description:

*Length.*—About 9 cm to 12 cm.

*Diameter.*—About 2 mm.

*Internode length.*—About 1.9 cm.

*Strength.*—Strong; flexible.

*Texture.*—Pubescent; coarse.

*Color.*—Close to 146B.

Foliage description:

*Arrangement.*—Opposite, simple.

*Length.*—About 6.7 cm.

*Width.*—About 3.2 cm.

*Shape.*—Ovate.

*Apex.*—Acute.

*Base.*—Attenuate to obtuse.

*Margin.*—Broadly create to dentate.

*Texture, upper and lower surfaces.*—Pubescent; coarse, rough.

*Venation pattern.*—Pinnate; arcuate.

*Color.*—Developing foliage, upper surface: Close to 146A to 146B. Developing foliage, lower surface: Close to 146B. Fully developed foliage, upper surface: Close to between N189A and 147A; venation, close to 146C. Fully developed foliage, lower surface: Close to 147A and 147B; venation, close to 146C.

*Petiole.*—Length: About 1.2 cm. Diameter: About 1.6 mm. Texture, upper surface: Pubescent; coarse, rough. Texture, lower surface: Smooth, nearly glabrous. Color, upper surface: Close to 146A. Color, lower surface: Close to 146B.

Flower description:

*Flower arrangement and habit.*—Solitary tubular flowers arranged in compact rounded axially umbels; flowers face mostly upward or outward. Freely flowering habit with potentially two inflorescences developing per node, each umbel with about 15 to 22 flowers.

*Natural flowering season.*—Spring until frost in the autumn; flowering continuous during this period.

*Flower longevity on the plant.*—About three to four days. Flowers not persistent.

*Fragrance.*—Pungently malodorous to lemon-like.

*Inflorescence height.*—About 1.5 cm.

*Inflorescence diameter.*—About 3.5 cm.

*Flowers.*—Appearance: Flared trumpet, salverform, corolla fused, four-parted; flowers sessile. Diameter: About 1.2 cm. Depth (height): About 1.1 cm. Throat diameter: About 1.5 mm. Tube length: About 1.1 cm. Tube diameter, base: About 1.1 mm.

*Flower buds.*—Length: About 1 cm. Diameter: About 3 mm. Shape: Elongate, oblong. Color: Base, close to 5C; mid-section, close to 22A to 22C and 33A to 33B; apex, close to 33A to 33B and 25A to 25B.

*Corolla.*—Arrangement: Single whorl of four to five fused petals. Petal lobe length: About 4.5 mm to 6 mm. Petal lobe width: About 4 mm to 7 mm. Petal lobe shape: Obovate. Petal lobe apex: Obtuse. Petal margin: Entire, undulate. Petal texture, upper and lower surfaces: Smooth, glabrous. Color: When opening, upper surface: Close to 17A, becoming closer to between N30A to N30D and 24A. When opening, lower surface: Close to 15B to 15D, becoming closer to between 22B and 35C. Fully opened, upper surface: Close to 17A, becoming closer to 34A to 34D, then close to 42A, then close to 51A to 51C; color eventually fading closer to between 35A to 35B and 26A. Fully opened, lower surface: Close to 13A, then close to 24B to 24D, then close to 26A; color eventually fading closer to N170C to N170D. Throat: Close to between 22A to 22B and 38D; towards the base, close to 5D. Tube: Close to 22B to 22C; towards the base, close to 5D.

*Calyx.*—Appearance: Short and narrow tubular calyx. Length: About 2.5 mm. Diameter: About 1.5 mm to 2 mm. Sepal apex: Acute. Sepal margin: Entire. Sepal texture, upper and lower surfaces: Smooth, glabrous. Sepal color, upper and lower surfaces: Close to 147C to 147D.

*Peduncles.*—Length: About 2.4 cm. Diameter: About 1.3 mm. Strength: Strong; flexible. Texture: Pubescent. Color: Close to 146A to 146B.

*Reproductive organs.*—Stamens: Quantity/arrangement: Four per flower, adnate to floral tube. Filament length: Less than 1 mm. Filament color: Close to 145D. Anther shape: Ovate; two-parted. Anther length: About 1 mm. Anther width: About 0.3 mm. Anther color: Close to 15A. Pollen amount: Moderate. Pollen color: Close to 15A. Pistils: Quantity: One per flower. Pistil length: About 4.5 mm. Stigma shape: Ovate to rounded. Stigma color: Close to 145C. Style length: About 2.9 mm. Style color: Close to 145D. Ovary color: Close to 144C. Fruits: Quantity: One per flower. Shape: Spherical. Diameter: About 6.5 mm. Texture: Glabrous, satiny. Color: Close to 103A. Seeds: Quantity: One per fruit. Length: About 5.4 mm. Diameter: About 3.7 mm. Color: Between N199A and N200B.

Temperature tolerance: Plants of the new *Lantana* have been observed to tolerate temperatures from about 5° C. to 8° C. to about 30° C.

Pathogen/pest resistance: Plants of the new *Lantana* have not been observed to be resistant to pests and pathogens common to *Lantanas*.

It is claimed:

1. A new and distinct *Lantana* plant named 'Weslamo' as illustrated and described.

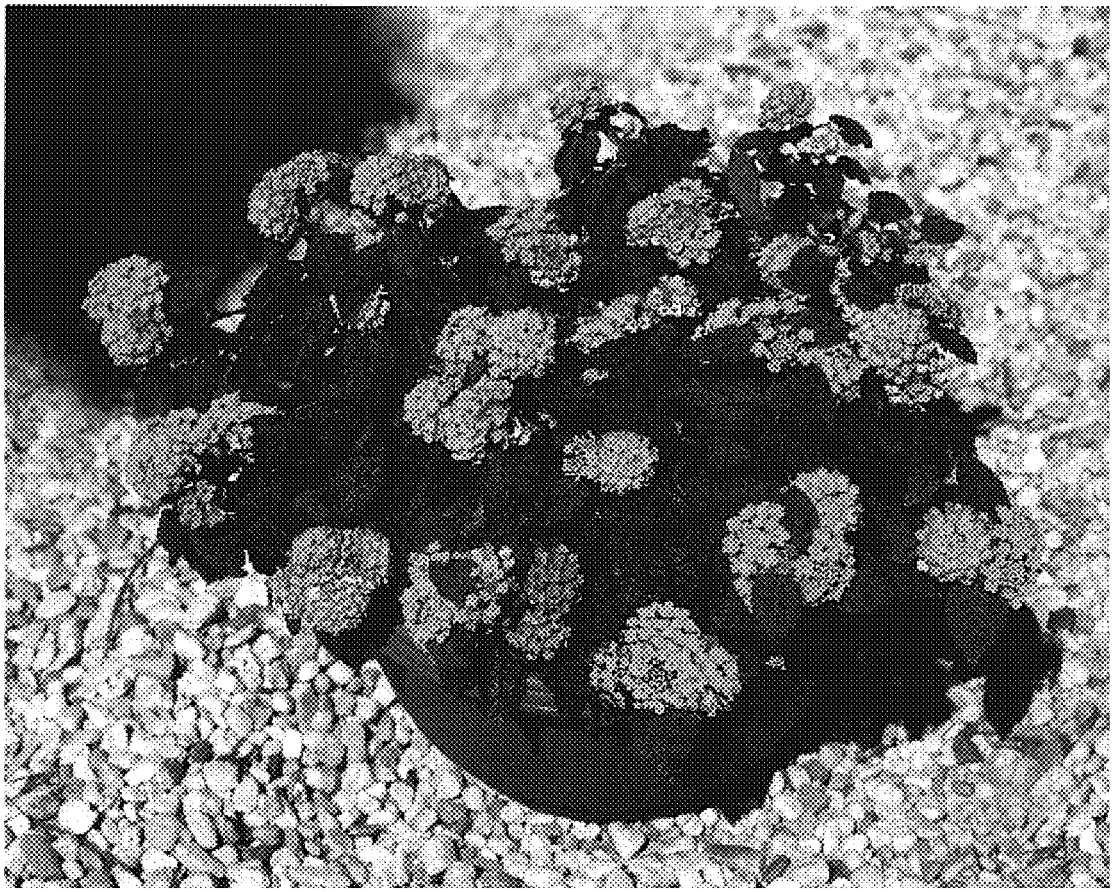
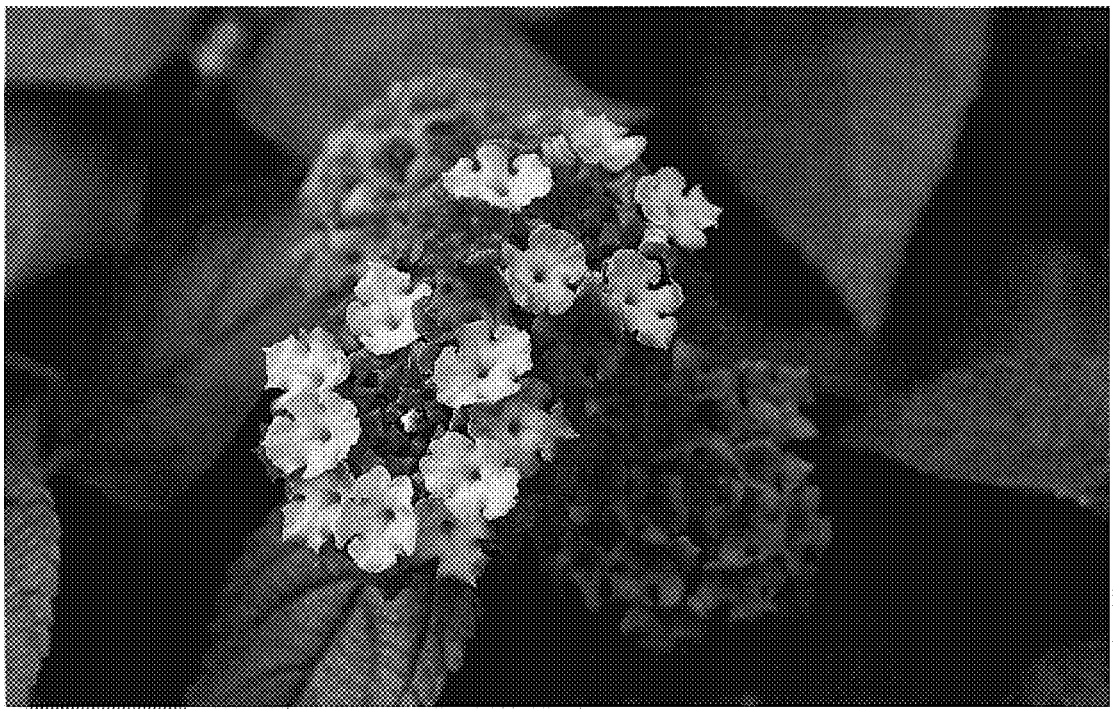

* * * * *